United States Patent [19]

Kubicek

[11] 4,288,627
[45] Sep. 8, 1981

[54] OXIDATION OF THIOLS EMPLOYING COBALT MOLYBDATE/TRIETHYLAMINE CATALYST

[75] Inventor: Donald H. Kubicek, Bartlesville, Okla.

[73] Assignee: Phillips Petroleum Company, Bartlesville, Okla.

[21] Appl. No.: 120,812

[22] Filed: Feb. 12, 1980

[51] Int. Cl.$^3$ .......................................... C07C 149/12
[52] U.S. Cl. ..................................................... 568/26
[58] Field of Search ......................................... 568/26

[56] References Cited

U.S. PATENT DOCUMENTS

| | | | |
|---|---|---|---|
| 2,574,884 | 11/1951 | Mertz et al. | 568/26 |
| 2,651,595 | 9/1953 | Moulthrop | 568/26 |
| 3,277,180 | 10/1966 | Bapseres et al. | 568/26 |
| 3,299,146 | 1/1967 | Gillette et al. | 568/26 |
| 3,308,166 | 3/1967 | Biensan et al. | 568/26 |
| 3,565,959 | 2/1971 | Lakase et al. | 568/26 |
| 3,978,137 | 8/1970 | Frame | 568/26 |
| 4,090,954 | 5/1978 | Ward | 568/26 |

OTHER PUBLICATIONS

E. E. Reid, Organic Chemistry of Bivalent Sulfur, I, 28–29, 118–120, (1958).
J.A.C.S., 70, Dec. 1948, pp. 4143–4150.

Primary Examiner—Donald G. Daus
Assistant Examiner—M. C. Eakin

[57] ABSTRACT

A thiol is oxidized to a corresponding disulfide employing a supported cobalt molybdate catalyst in combination with a liquid tertiary amine. 2-propanethiol is converted to diisopropyl disulfide with conversions of the order of 94% and selectivities of the order of 98%.

7 Claims, No Drawings

OXIDATION OF THIOLS EMPLOYING COBALT MOLYBDATE/TRIETHYLAMINE CATALYST

BRIEF SUMMARY OF THE INVENTION

A supported cobalt molybdate catalyst is employed together with a liquid tertiary amine to oxidize a thiol (mercaptan) to a disulfide. Good selectivity and conversion are obtained when oxidizing, e.g., 2-propanethiol to diisopropyl disulfide when a 94% conversion with 98% selectivity is obtained.

DETAILED DESCRIPTION

This invention relates to the production of a disulfide. In one of its aspects, the invention relates to the oxidation of a thiol to a disulfide. In another of its aspects, the invention relates to a catalytic combination for the conversion of a thiol to a disulfide.

In one of its concepts, the invention provides a process for the conversion of a thiol to a corresponding disulfide with high conversion and high selectivity by oxidizing the same as with air or oxygen in the presence of a combination of cobalt molybdate on a support and a liquid tertiary amine.

Organic disulfides have varied applications ranging from intermediates for insecticides, herbicides and rodent repellents to additives in greases and diesel fuels. The synthesis of such disulfides is well known and generally is based on the corresponding thiols (mercaptans). One such synthesis is reported in U.S. Pat. No. 2,574,884, issued Nov. 13, 1951, wherein tertiary alkanethiols are oxidized with oxygen to sulfides and disulfides in the presence of alumina-based catalysts like chromia, vanadia, and magnetic iron oxide. The thiol conversions are low and other sulfide products (e.g. trisulfides) are formed. U.S. Pat. No. 3,340,324 describes the preparation of di-tert-butyl disulfide from 2-methyl-2-propanethiol and elemental sulfur in the presence of an alcohol and an alkali metal hydroxide. In J.A.C.S. 70, 4143-4150 (1948) it is disclosed that mercaptans in the presence of elemental sulfur are converted to disulfides when a trace of an amine is present. Each of the above references and others have a common disadvantage, namely low thiol conversions and/or low disulfide selectivity.

It is desirable because of economic and chemical importance to prepare disulfide in more nearly quantitative selectivity and conversion.

It is an object of this invention to prepare a disulfide. It is another object of this invention to provide a catalyst for the oxidation of a mercaptan to the corresponding disulfide. It is a further object of this invention to provide a process for the conversion in near quantitative yield and quantitative selectivity of a mercaptan to a corresponding disulfide.

Other aspects, concepts, objects, and several advantages of the invention are apparent from the study of this disclosure and the claims.

According to the invention, a mercaptan, which can have a formula as herein given, is subjected to oxidation as with oxygen or air to prepare a corresponding disulfide, employing as catalyst, a supported cobalt molybdate and a liquid tertiary amine.

Thiols useful in this invention are those materials represented by the formula

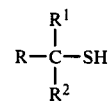

wherein R, $R^1$, and $R^2$ can be hydrogen or an alkyl or cycloalkyl radical ranging from 1 to 20 carbon atoms with the proviso that R and $R^1$ taken together can be an alkylene radical having from 5 to 10 carbon atoms. For example, materials to be used that correspond to the above formula can be, but not limited to:

methanethiol
ethanethiol
1-propanethiol
2-propanethiol (isopropyl mercaptan)
1-butanethiol
2-butanethiol
2-methyl-2-propanethiol (tert-butyl mercaptan)
1-pentanethiol
2-pentanethiol
3-pentanethiol
3-methyl-2-butanethiol
3-methyl-2-propanethiol
1-hexanethiol
2-hexanethiol
3-hexanethiol
2-methyl-2-pentanethiol
cyclohexanethiol
1-methylcyclohexanethiol
4-methylcyclohexanethiol and the like, and mixtures thereof. Primary and secondary thiols are preferred although tertiary thiols are also useful.

The catalyst system useful in this invention is comprised of a combination of cobalt molybdate on a support and a liquid tertiary amine. Any supported cobalt molybdate catalyst is within the scope of this invention. A typical catalyst would contain about 3 to 4 wt. % cobalt oxide and about 12 to 18 wt. % molybdenum oxide on a support such as α-alumina, γ-alumina, alumina-silica, charcoal, silica, magnesium oxide, silica-carbon and the like. The specific cobalt molybdate catalyst employed to reduce to practice the current invention is HDS-2 (a hydrodesulfurization catalyst) from American Cyanamid Co. The approximate composition of this catalyst is given as:

| HDS-2 (American Cyanamid) | |
| --- | --- |
| Ingredient | Wt. % |
| Cobalt oxide | 3-4 |
| Molybdenum oxide | 15-16 |
| Sodium oxide | 0.4 |
| Iron oxide | 0.05 |
| Alumnia (support) balance | |

The tertiary amines useful as co-catalysts in this invention are those materials represented by the formula

where $R^3$ can be any alkyl radical having 1 to 6 carbon atoms. Each alkyl radical can be the same or different. For example, materials to be used that correspond to the above formula can be, but not limited to:

trimethylamine
triethylamine tri-n-propylamine
tri-n-butylamine
tri-n-pentylamine
tri-n-hexylamine
methyldiethylamine
ethyldipropylamine
ethyldimethylamine and the like, and mixtures thereof. The amine must be easily separable from the products, for example, by distillation or as a residue from a distillation. The amount of catalyst used was 0.2 grams HDS-2 and 7 milliliters (5.1 grams) triethylamine per 50 milliliters of either 2-propanethiol or 2-methyl-2-propanethiol. Although these amounts are ordinarily preferred, it is within the scope of the invention to use different amounts, for example, in the ranges of 0.1 gram to about 1 gram HDS-2 catalyst and 1 to 10 milliliters of liquid tertiary amine, and 25 to 100 milliliters of alkane or cycloalkanethiol.

Air or oxygen can be and has been used in the process of the invention. When air or oxygen is bubbled through the reaction mixture, the rate of air or oxygen passage should be only fast enough so as not to remove any reactant. If the gas is not bubbled through but only reacted within a sealed system it is preferred to have a nitrogen blanket and add oxygen as it is absorbed. This will avoid explosive mixtures from forming. The rate of air or oxygen flow through the system is arbitrarily selected at 2 to 4 scf/hr. (standard cubic feet/hour).

Solvents are optional in this invention since the reaction works equally well without them. Also, solvents require an extra separation step. Nevertheless, the use of solvents is within the scope of this invention. Alcohols having 1 to 10 carbon atoms are the preferred solvents. Examples of some suitable alcohols are methyl alcohol, ethyl alcohol, propyl alcohol, isopropyl alcohol, butyl alcohol, decyl alcohol and the like and mixtures thereof.

Conditions suitable in the current invention are shown as follows:

|  |  | Broad | Preferred |
|---|---|---|---|
| Temperature, | °F. | 60–350 | 70–250 |
|  | °C. | 15.6–176.7 | 21.1–121.1 |
| Pressure, | psig | 10–1000 | 25–500 |
|  | MPa | 0.069–6.895 | 0.172–2.337 |

The following examples serve to illustrate the invention. Examples III and IV are according to the invention.

EXAMPLE I

This example is a control run demonstrating the use of solid sodium hydroxide in alcohol with cobalt molybdate on alumina for the air oxidation of 2-propanethiol to diisopropyl disulfide. The system works well to give good conversion and selectivity. However, a product and solvent phase form which require subsequent separation. In addition, the system leaves a kettle residue which when carried out on an industrial scale must be waterwashed, thus, making an extra step. To a 300 milliliter 316 stainless steel autoclave equipped with a stirrer, internal cooling coils, overhead condenser, back pressure regulator and an air addition tube was charged 1 gram (0.025 moles) solid sodium hydroxide powder, 0.2 gram of cobalt molybdate on alumina catalyst (HDS-2), 25 milliliters (19.8 grams) methyl alcohol, and 50 milliliters (40.3 grams, 0.497 moles) 2-propanethiol (isopropyl mercaptan). After closing the reactor, the agitator was started and the system pressured to 300 psig (2.068 MPa) with air at about 25° C. (77° F.). An air flow was then started through the reaction mixture (e.g. below the liquid surface) at such a rate that a minimum amount of alcohol and mercaptan were carried overhead through the condenser (2.5 cubic feet/hr.). The reactor temperature was allowed to rise to about 54°–60° C. (130°–140° F.) due to the heat generated by the reaction. This temperature was then maintained by the addition of cooling water through the coils. After 20 minutes, the reaction mixture was cooled to about 25° C. vented and transferred to a separatory funnel. Two liquid phases formed. Each of these phases was analyzed by GLC using a 12 ft × ¼ in. column packed with 10% SE 30 silicone rubber on 60–80 mesh Chromosorb P that had been previously mineral acid washed and dried. The top phase (27 milliliters) contained 93.9 vol. % methyl alcohol, 3.8 vol. % diisopropyldisulfide and 2.3 vol. % heavies. The bottom phase (37 milliliters) contained 1.4 vol. % methyl alcohol, 98 vol. % diisopropyl disulfide and 0.6 vol. % heavies. Based on these analyses, there was obtained a 98% conversion of 2-propanethiol with a 97% selectivity of diisopropyldisulfide.

EXAMPLE II

This example is a control run using a liquid organic base instead of the cobalt-molybdate (HDS-2)/ sodium hydroxide catalyst of Example I. The results show that the liquid organic base is not as good a catalyst as the cobalt-molybdate/sodium hydroxide catalyst. The procedure described in Example I was repeated except 7 milliliters (5.1 grams, 0.05 moles) of triethylamine was used in place of sodium hydroxide and HDS-2 and the methyl alcohol was replaced with isopropyl alcohol. The reaction required some external heating (54.4° C., 130° F.). After 3 hours reaction time, the reaction mixture (63 milliliters) was cooled and analyzed as previously described. There was obtained a 34% conversion with a 97.2% selectivity to the desired diisopropyl disulfide.

EXAMPLE III—INVENTION RUN

This example shows when HDS-2 catalyst is employed along with the liquid organic base the conversion of the thiol reactant is greatly increased. The procedure described in Example I was repeated except the catalyst used was 0.2 gram HDS-2 plus 7 milliliters triethylamine. Also, isopropyl alcohol was used in place of methyl alcohol. The reaction was very exothermic and the temperature had to be controlled with internal cooling to maintain a temperature below about 52° C. (125° F.). After 1.25 hrs., the reaction mixture was cooled and analyzed. There was obtained a 94% conversion of the 2-propanethiol with 98% selectivity to diisopropyldisulfide. When the reaction was repeated using only 3.5 milliliters triethylamine plus 0.2 gram HDS-2 there was obtained a slightly less conversion, namely 83%. The selectivity was still 98%. This latter result indicates that as the amount of amine is decreased the conversion is lowered. This suggests that if only HDS-2 was used as the catalyst the % conversion would be very low.

EXAMPLE IV—INVENTION RUN

This example shows that when the catalyst system HDS-2/triethylamine is employed, solvent is not needed to obtain a high yield and conversion. The reaction product mixture contained only one liquid phase, thus, eliminating the need for liquid-liquid phase separation. The solid catalyst, HDS-2, could be removed merely by decantation or filtration. The procedure described in Example III was repeated except no alcohol solvent was employed. The analysis indicated a 98% conversion of the 2-propanethiol with a 98% selectivity to the desired diisopropyl disulfide.

EXAMPLE V

This example reports a run employing a tertiary alkanethiol. The results indicate the catalyst system HDS-2/triethylamine works with tertiary alkanethiol both with and without an alcohol solvent but not as successfully as when secondary alkanethiols are employed. The results also show high conversion and high selectivity when tertiary alkanethiols are air oxidized in the presence of HDS-2/sodium hydroxide. The procedure described in EXAMPLES I, III, and IV was repeated except that 2-methyl- 2-propanethiol (tertiary butyl mercaptan) was used in place of 2-propanethiol (isopropyl mercaptan). These results are listed in Table I.

TABLE I

Conversion of 2-Methyl-2-Propanethiol to Ditertiary-Butyl Disulfide

| Run No. | t-C₄SH,mL | CH₃OH,mL | HDS-2,g | NaOH,g | Et₃N,mL | % RSH Conversion | % RSSR Selectivity |
|---|---|---|---|---|---|---|---|
| Va | 50 | 25 | 0.2 | 1.0 | — | 98 | 97 |
| Vb | 50 | 25 | 0.2 | — | 7.0 | 65 | 83 |
| Vc | 50 | — | 0.2 | — | 7.0 | 27 | 85 |

SUMMARY

The examples herein described are summarized in Table II. These results show that secondary mercaptans like 2-propanethiol can be readily converted to diisopropyl disulfide using a cobalt-molybdate on alumina catalyst and a liquid tertiary amine co-catalyst in the absence of a solvent (Example IV). The advantage of such a run over a control run using a solvent and a solid alkali metal hydroxide co-catalyst (Example I) is in the subsequent separation and recovery steps. The process of the invention does not require solvent separation. Nor is there incurred any significant loss of co-catalyst by discarding it in a waste water phase. The data also shows similar results with tertiary mercaptans, e.g., 2-methyl-2-propanethiol, although the selectivity and conversions are significantly less, (Example V).

high selectivity to a corresponding disulfide employing for the purpose a supported cobalt molybdate catalyst in combination with a tertiary amine liquid under the conditions of operation.

I claim:

1. A process for the conversion of a thiol represented by the formula

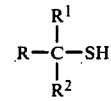

wherein R, R¹, and R² can be hydrogen, alkyl, or cycloalkyl containing from 1 to 20 carbon atoms, R and R¹ taken together can be an alkylene radical having from 5 to 10 carbon atoms to a corresponding disulfide which comprises subjecting the same to oxidation conditions including air or oxygen-containing gas in the presence of a cobalt oxide molybdenum oxide catalyst on a support and a liquid tertiary amine represented by the formula

where R³ can be any alkyl radical having 1 to 6 carbon atoms.

2. A process according to claim 1 wherein the catalyst contains from about 3 to about 4 weight percent cobalt oxide and about 12 to about 18 weight percent molybdenum oxide on a suitable support.

3. A process according to claim 2 wherein the molybdenum oxide and cobalt oxide is on a support selected from alpha-alumina, gamma-alumina, alumina-silica, charcoal, silica, magnesium oxide, silica-carbon, and mixtures thereof.

4. A process according to claim 1 wherein the catalyst has the following approximate weight percent composition:

TABLE II

Summary. Conversion of Alkanethiols to Dialkyl Disulfides

| Example No. | RSH,50mL | ROH,mL | HDS-2,g | NaOH,g | Et₃N,mL | % RSH Conversion | % RSSR Selectivity |
|---|---|---|---|---|---|---|---|
| I | i-C₃SH | 25² | 0.2 | 1 | — | 98 | 97 |
| II | i-C₃SH | 25³ | — | — | 7 | 34 | 97 |
| IIIa | i-C₃SH | 25³ | 0.2 | — | 7 | 94 | 98 |
| IIIb | i-C₃SH | 25³ | 0.2 | — | 3.5 | 83 | 98 |
| IV | i-C₃SH | — | 0.2 | — | 7 | 98 | 98 |
| Va | t-C₄SH | 25² | 0.2 | 1 | — | 98 | 97 |
| Vb | t-C₄SH | 25² | 0.2 | — | 7 | 65 | 83 |
| Vc | t-C₄SH | — | 0.2 | — | 7 | 27 | 85 |

¹Et₃N is triethylamine. i-C₃SH is 2-propanethiol. t-C₄SH is 2-methyl-2-propanethiol.
²Methyl alcohol.
³Isopropyl alcohol.

Reasonable variation and modification are possible within the scope of the foregoing disclosure and the appended claims to the invention the essence of which is that a thiol is converted with high conversion and Cobalt oxide    3–4

-continued

| Molybdenum oxide | 15-16 |
| Sodium oxide | 0.4 |
| Iron oxide | 0.05 |
| Alumnia (support) | balance |

5. A process according to claim 1 wherein the thiol is at least one selected from

| | |
|---|---|
| methanethiol | 2-hexanethiol |
| ethanethiol | 3-hexanethiol |
| 1-propanethiol | 2-methyl-2-pentanethiol |
| 2-propanethiol | cyclohexanethiol |
| (isopropyl mercaptan) | |
| 1-butanethiol | 1-methylcyclohexanethiol |
| 2-butanethiol | 4-methylcyclohexanethiol |
| 2-methyl-2-propanethiol | |
| (tert-butyl mercaptan) | |
| 1-pentanethiol | |
| 2-pentanethiol | |
| 3-pentanethiol | |
| 3-methyl-2-butanethiol | |

-continued 3-methyl-2-propanethiol
1-hexanethiol

6. A process according to claim 1 wherein the tertiary amine is at least one selected from
 trimethylamine
 triethylamine
 tri-n-propylamine
 tri-n-butylamine
 tri-n-pentylamine
 tri-n-hexylamine
 methyldiethylamine
 ethyldipropylamine
 ethyldimethylamine 7. A process according to claim 1 wherein the cobalt molybdate catalyst, including support, is employed in the range of from about 0.1 g to about 1 g and the tertiary amine is in the range of from about 1 to about 10 mL employed to convert from about 25 to about 100 mL of the thiol.

* * * * *